(12) United States Patent
Stone

(10) Patent No.: US 6,630,354 B2
(45) Date of Patent: Oct. 7, 2003

(54) CHROMATOGRAPHY USING MICROWAVE PULSING

(76) Inventor: Mark A. Stone, 240 Prospect Ave., Apt. 293, Hackensack, NJ (US) 07601

( * ) Notice: Subject to any disclaimer, the term of this patent is extended or adjusted under 35 U.S.C. 154(b) by 0 days.

(21) Appl. No.: 09/997,919

(22) Filed: Nov. 30, 2001

(65) Prior Publication Data

US 2003/0109053 A1 Jun. 12, 2003

(51) Int. Cl.⁷ .............................................. G01N 30/28
(52) U.S. Cl. .................... 436/161; 73/61.52; 210/198.2; 210/656; 250/435; 250/492.1; 422/70
(58) Field of Search ............................ 436/161; 422/70; 210/198.2, 656; 73/61.52; 250/492.1, 435

(56) References Cited

U.S. PATENT DOCUMENTS 4,204,423 A * 5/1980 Jordan
6,061,926 A * 5/2000 Pare et al.
6,157,015 A * 12/2000 Gaisford et al.

* cited by examiner

*Primary Examiner*—Jan Ludlow
(74) *Attorney, Agent, or Firm*—Weiner & Burt, P.C.; Irving M. Weiner; Pamela S. Burt

(57) ABSTRACT

A method of using microwave-induced dielectric polarization to enhance the diffusivity of a liquid or a supercritical fluid mobile phase in chromatography, while having essentially no effect on other physical properties of the mobile phase.

13 Claims, No Drawings

CHROMATOGRAPHY USING MICROWAVE PULSING

The present invention relates generally to a method of improving chromatography using microwave radiation. More particularly, the present invention relates to a method of improving chromatography of a fluid containing an analyte by the use of microwave-induced dielectric polarization.

BACKGROUND OF THE INVENTION

There are three major chromatographic techniques: high performance liquid chromatography (HPLC), supercritical fluid chromatography (SFC), and gas chromatography (GC). The speed of these separation methods increases in the order GC>SFC>HPLC. The reason for this being the differences in the diffusivities of the respective mobile phases, and hence, of the analytes within the mobile phases. This difference in speed is especially notable with open-tubular columns. Open-tubular columns with internal diameters in the range of 0.25 to 0.53 mm are typically used for gas chromatography; however, these same columns would result in excessively long analysis times with either SFC or HPLC. This can be offset by using columns of narrower ID: hence open-tubular SFC and HPLC are typically done with columns of 0.04 to 0.05 mm ID. Even then, analysis is slow and these narrow ID columns present several additional difficulties. They have a very low capacity for analyte material, the volume of sample that can be injected is limited which lessens the mass sensitivity, and very small volume detector cells need to be used. It is for these reasons that open-tubular columns are seldom used for HPLC or SFC.

This is unfortunate as open-tubular columns have many inherent advantages over packed columns including better efficiency due to the lack of Eddy diffusion and the smaller stationary phase film thickness. The smaller volume of mobile phase typically used with open-tubular column separations results in sharper chromatographic peaks, further increasing efficiency and allowing for better sensitivity. The lower mobile phase flow rates of these columns also make it easier to interface with ionization type detectors: most importantly mass spectrometers. Finally, open-tubular columns have a much smaller pressure drop across them, allowing longer columns to be used.

As stated above, much faster analysis is possible with gas chromatography. However, the downside of gas chromatography is that the mobile phase has no solvating power and, therefore, only analytes that possess some volatility can be separated by the technique. Supercritical fluid chromatography can separate a wider range of analytes as the mobile phase has some solvating power. However, liquid chromatography is by far the most versatile chromatographic method. Virtually all analytes are amenable to liquid chromatography including macromolecules such as synthetic polymers, proteins, and carbohydrates.

If it were possible to increase the diffusivity of a liquid mobile phase, the resulting technique would offer the best of both worlds. The high diffusivity would allow for faster analysis and would make it possible to reap the benefits offered by open-tubular columns (of moderate to large internal diameters). However the liquid would still possess its high solvating power, making it possible to separate virtually any analyte. Previously, this has been accomplished by conducting liquid chromatography at highly elevated temperatures (up to 150° C.). However, there are several disadvantages to this approach. First, the mobile phase must be preheated prior to reaching the column by passing through a certain length of tubing, maintained in an oven. There is a delay associated with this. In order that fast analysis could still be obtained, the analytes were delivered by a separate line—much shorter and with a narrower ID—that teed into the mobile phase line. Hence, there was a significant dilution of the analytes resulting in a loss of efficiency and sensitivity. Secondly, additional hardware was required in order to maintain pressure in the column so that the solvents did not boil at the elevated temperatures and also to cool the mobile phase down prior to reaching the detector. Thirdly, the analyst is limited in the types of stationary phases that can be used. Lastly, this approach will be problematic if working with analytes that are not temperature stable.

It is a desideratum of the present invention to avoid the animadversions of the above-mentioned existing techniques.

SUMMARY OF THE INVENTION

The present invention provides a novel and unique method of improving chromatography of a fluid containing an analyte, comprising the steps of: commencing a run of said fluid containing said analyte through a chromatoghaphic separation column; and subjecting said fluid containing said analyte to microwave radiation.

It is an object of the present invention to provide a more desirable approach to elevating the diffusivity of a liquid mobile phase than has been used previously. That is, to make use of the phenomenon of microwave-induced dielectric polarization.

This object and other features and advantages of the present invention will become apparent to those persons skilled in this particular area of technology and to others after reading the present patent application.

DETAILED DESCRIPTION OF THE INVENTION

Electromagnetic radiation of any kind consists of an electric field and a magnetic field, at right angles to one another, continually increasing and decreasing in magnitude. The dielectric polarization phenomenon can be understood by considering that when the electric field increases in size, molecules that contain a dipole are caused to align with the electric field. When the field subsides, the molecules randomize. At 2450 MHz (the frequency typically used in household and laboratory microwave systems) this alignment and randomization occurs $4.9 \times 10^9$ times per second.

Although this phenomenon is often used for heating liquids, it is possible to increase the diffusivity of a liquid while having a negligible effect on its temperature by pulsing with microwave energy for very short intervals. There are two alternative approaches that can be used to increase the mobile phase diffusivity. However, these methods also result in other, undesirable, changes to the mobile phase. Simple heating of a liquid mobile phase carries with it a handful of disadvantages, as was discussed above. The other approach is simply to change techniques so that a higher diffusivity mobile phase is used, i.e., going from liquid chromatography to gas chromatography. The problem here, of course, is that on going from a liquid to a gas there is a drastic reduction in solvating power, and hence, the range of analytes that can be handled by the technique. Conversely, with the present invention, it is possible to increase the diffusivity of a liquid mobile phase, and reap all the resultant advantages, while having a minimal effect on other properties of the mobile phase, such as temperature or solvating power.

Several analyses were undertaken to obtain proof-of-concept that the dielectric polarization phenomenon could, in fact, be used to sharpen chromatograhic peaks in an HPLC analysis.

A microwave capable of delivering very short pulses of radiation was not available, hence, for purposes of preliminary evaluation a Samsung domestic 600 Watt microwave, at the standard frequency of 2450 MHz, was used. As this system is not capable of any type of power cycling, it was manually turned on and off throughout the analysis. A Hewlett-Packard (Wilmington, Del.) Model 1050 HPLC pump was used along with a model 1050 autosampler and a model 1050 multivariable wavelength UV detector. Methanol and water (no buffers or additives) were used as the mobile phase. Two different gradients were used. For all analyses 10 uL were injected, a flow rate of 1 mL/min was used, and a wavelength of 205 nm was set for detection. Data were collected on a Hewlett-Packard integrator model 3394A. All height/area values reported below were calculated by the integrator.

A 25 cm IonPac NS-1 column with a 4 mm internal diameter was obtained from Dionex (Sunnyvale, Calif.) and used for all analyses. The column contained 5 um polystyrene divinylbenzene particles. Because this column is designed for ion chromatography, it is made of peek (poly-ether-ether-ketone), not metal. This was important as metal would have been problematic in the microwave oven.

The stock solution used contained 2-naphthol at 307 ug/mL and benzene at 566 ug/mL in methanol.

The first evaluation was a comparison between a run without microwave radiation, and a run where the microwave was turned on every 10 seconds for an interval of approximately one second. The LC gradient used was as follows: 80/20 methanol/water for 1.7 minutes, ramped to 87/13 methanol/water at three minutes and held there for the rest of the run. The data are presented below. Peak heights are used as a quantitative measure of peak sharpness, or efficiency. To normalize for any variability in injection volume, or for changes in concentration due to evaporation of solvent, height values are reported relative to the peak area.

The data, presented in Table I, show a clear increase in peak sharpness when radiation was applied.

TABLE I

| | Peak Height/Peak Area | |
|---|---|---|
| | Naphthol | Benzene |
| Microwave Off | 1.18 | 1.03 |
| ~1 Second pulse every 10 seconds | 1.79 | 1.46 |
| % Increase | 52% | 42% |

The same experiment was repeated and similar results were obtained, though the change was somewhat larger for the benzene peak in the second trial, see Table II.

TABLE II

| | Peak Height/Peak Area | |
|---|---|---|
| | Naphthol | Benzene |
| Microwave Off | 1.26 | 1.09 |
| ~1 Second pulse every 10 seconds | 1.86 | 1.73 |
| % Increase | 48% | 59% |

When shorter pulses were used (approximated at ⅓ of a second) at ten second intervals, less of an effect was observed; however, when these short pulses were applied more closely together, increasingly sharper peaks were observed. The data are presented in Table III below. A different gradient was used here to better ensure focusing of the analytes at the head of the column prior to the separation: in this experiment 70/30 methanol/water for 1.5 minutes, ramped to 90/10 methanol/water at seven minutes and held there for the remainder of the run. For this reason the peaks without microwave radiation were somewhat sharper than those obtained previously.

TABLE III

| | Peak Height/Peak Area | |
|---|---|---|
| | Naphthol | Benzene |
| Microwave Off | 1.56 | 1.28 |
| ~⅓ of a second pulse every 10 seconds | 1.74 | 1.34 |
| ~⅓ of a second pulse every other second | 2.45 | 1.86 |
| % Increase (pulse every other second vs no radiation) | 57% | 45% |

Due to the crude nature of the system used, it was impossible to deliver the very short pulses of radiation that would have been ideal for this application. As a result, some heating of the mobile phase did occur. In order to confirm that the sharpening of peaks was due to the dielectric polarization phenomenon, and not to the temperature change, the column was placed in a conventional oven and heated. The following data were obtained with the oven set at 75° C. This setting resulted in retention times very similar to those obtained in the run where pulsing was applied every other second: indicating that the temperature of the mobile phase was comparable to that during this run. As seen in Table IV, the height to area ratio obtained were somewhat elevated in comparison to the run with no heating or radiation. However, the change was only ⅕ of that obtained with microwave pulsing every other second. This provided clear evidence that the dielectric polarization phenomenon was the primary cause of the sharpening of the peaks.

TABLE IV

| | Peak Height/Peak Area | |
| --- | --- | --- |
| | Naphthol | Benzene |
| Column in oven at 75EC | 1.70 | 1.43 |
| % Increase vs no radiation or heat | 9% | 12% |

It is important to keep in mind that the equipment used to generate these data were not ideal in many respects. Most important was the inability to deliver very short pulses of radiation with a greater number of pulses per unit time. The data presented in Table III demonstrate the importance of frequent pulsing. Most systems sold commercially for extraction or digestion are capable of delivering pulses of radiation that are orders of magnitude less, in duration, than the pulses that could be applied with the domestic microwave used in this work. It should be noted, however, that when the power percentage is increased on these systems the on-time-interval, i.e., the period of time that the magnetron is turned on, increases. It may be that the ideal situation would be to use a pulse generator. This would allow the analyst to increase the number of pulses delivered per unit time instead of increasing the duration of the pulses. Short pulses are ideal from the standpoint of minimizing heat generation in the column.

The present invention would allow faster and more efficient analyses with packed column reversed-phase HPLC. The technique would also be applicable to packed column normal-phase LC as well as supercritical fluid chromatography (SFC) separations. The technique is expected to make separations with open-tubular columns much more feasible for both HPLC and SFC. Of course, carbon dioxide is an extremely inefficient absorber of microwave radiation, hence, either the analytes themselves would need to have some polarity or a small quantity of a polar modifier would need to be present in the fluid for SFC applications.

It should be noted that, although we have discussed the problems associated with heating of the mobile phase, and have emphasized the ability of the current technique to result in minimal generation of heat, there may be cases where a degree of heating would be desirable. The technique advocated here offers the flexibility of being applicable either with negligible heat generation or with a substantial degree of heat generation: this is controlled simply by changing the duration of the microwave pulses.

The technique is not advocated for gas chromatography for several reasons. The mobile phases typically used in GC are generally cheap, non-polar, essentially non-toxic, have a high ionization potential (good for mass spec) and do not support combustion (important for FID). Going to a polar gas would likely compromise most or all of these advantages. It should also be mentioned that gases have a high diffusivity to begin with and it is questionable whether substantial additional benefit could be generated to make it worth the effort. However, an interesting GC application that would make sense is in headspace analysis. Because the coupling of microwave radiation with non-polar material is very inefficient it would be possible to achieve selective thermal excitation of polar analytes from a non-polar matrix. An example of this would be if one were interested in analyzing oxygenated or nitrogenated material in a petroleum sample. Microwave radiation would make it possible to thermally excite this material and drive it into the headspace while having essentially no effect on the petroleum matrix.

There have been described hereinabove only some unique and novel preferred embodiments of the present invention which can be implemented in many different ways. It should be understood that many changes, modifications, variations, and other uses and applications will become apparent to those persons skilled in this particular area of technology and to others after having been exposed to the present patent application.

Any and all such changes, modifications, variations, and other uses and applications which do not depart from the spirit and scope of the present invention are therefore covered by and embraced within the present invention and the patent claims set forth hereinbelow.

What is claimed is:

1. A method of improving chromatography of a fluid containing an analyte, comprising the steps of:

commencing a run of said fluid containing said analyte through a chromatographic separation column; and directly subjecting said fluid containing said analyte to microwave radiation to increase diffusivity of said fluid while having a negligible effect upon the temperature of said fluid by pulsing said microwave radiation to deliver a plurality of pulses of microwave radiation.

2. The method according to claim 1, wherein:

said microwave radiation step is controlled in a predetermined manner in order to produce microwave-induced dielectric polarization.

3. The method according to claim 1, wherein:

said microwave radiation step is controlled in a predetermined manner in order to deliver said pulses of radiation.

4. The method according to claim 2, wherein:

said microwave radiation step is controlled in a predetermined manner in order to deliver said pulses of radiation.

5. The method according to claim 1, wherein;

said microwave radiation is controlled in a predetermined manner in order to deliver a predetermined plurality of said pulses of radiation per unit time.

6. The method according to claim 2, wherein:

said microwave radiation step is controlled in a predetermined manner in order to deliver a predetermined plurality of said pulses of radiation per unit time.

7. The method according to claim 3, wherein:

said microwave radiation step is controlled in a predetermined manner in order to deliver a predetermined plurality of said pulses of radiation per unit time.

8. The method according to claim 4, wherein:

said microwave radiation step is controlled in a predetermined manner in order to deliver a predetermined plurality of said pulses of radiation per unit time.

9. The method according to claim 1, wherein:

said chromatography comprises liquid chromatography; and said radiation step increases the diffusivity of a liquid mobile phase.

10. The method according to claim 2, wherein:

said chromatography comprises liquid chromatography; and said radiation step increases the diffusivity of a liquid mobile phase.

11. The method according to claim 1, wherein:

said chromatography comprises packed column normal-phase liquid chromatography.

12. The method according to claim 1, wherein:

said chromatography comprises a supercritical fluid chromatography separation.

13. The method according to claim 1, wherein: said method is applicable to any mode of chromatography with a liquid or a supercritical fluid mobile phase.

* * * * *